US012636451B2

(12) United States Patent
    Trivedi

(10) Patent No.:  US 12,636,451 B2
(45) Date of Patent:     May 26, 2026

(54) AIRWAY MANAGEMENT DEVICE WITH CURVED STYLET

(71) Applicant: Jitin N. Trivedi, Ankleshwar (IN)

(72) Inventor:  Jitin N. Trivedi, Ankleshwar (IN)

( * ) Notice:    Subject to any disclaimer, the term of this patent is extended or adjusted under 35 U.S.C. 154(b) by 521 days.

(21) Appl. No.:  17/614,377

(22) PCT Filed:  Jul. 28, 2020

(86) PCT No.:  PCT/IN2020/050656
    § 371 (c)(1),
    (2) Date:  Nov. 26, 2021

(87) PCT Pub. No.:  WO2021/038579
    PCT Pub. Date: Mar. 4, 2021

(65)          Prior Publication Data
    US 2022/0218930 A1      Jul. 14, 2022

(30)      Foreign Application Priority Data
    Aug. 31, 2019    (IN) .............................. 201921035210

(51) Int. Cl.
    *A61M 16/04*          (2006.01)
(52) U.S. Cl.
    CPC .  *A61M 16/0488* (2013.01); *A61M 2205/0216* (2013.01); *A61M 2205/0266* (2013.01); *A61M 2205/36* (2013.01); *A61M 2205/587* (2013.01); *A61M 2210/0625* (2013.01)
(58) Field of Classification Search
    CPC .......... A61M 16/0418; A61M 16/0486; A61M 16/0488
    See application file for complete search history.

(56)              References Cited

U.S. PATENT DOCUMENTS 3,996,939  A  *  12/1976  Sheridan  ...........  A61M 16/0488
                                              128/207.14
    4,512,765  A  *  4/1985  Muto  ......................  A61M 1/85
                                              604/530
    4,529,400  A  *  7/1985  Scholten  ...........  A61M 25/0138
                                              128/207.14
    4,672,960  A  *  6/1987  Frankel  .............  A61M 16/0488
                                              128/207.14

(Continued)

FOREIGN PATENT DOCUMENTS

CN        107007916        8/2017
    CN        207055724  U  *  3/2018
                    (Continued)

*Primary Examiner* — Kathryn E Ditmer
(74) *Attorney, Agent, or Firm* — Hodgson Russ LLP

(57)              ABSTRACT

The present invention relates to a system (100) for managing an airway. The system comprises an elongated tube (102) having a proximal end (104), and a distal end (106), and defines a first lumen (108), extending between the proximal end (104) and the distal end (106), having a passageway and a second lumen (110), positioned adjacent to the first lumen (108), extending between the proximal end (104) and the distal end (106). The system (100) further comprises a stylet (112) that is disposed at least partially into and removable from the first lumen (108), wherein the stylet (112) is used for steering and guiding the elongated tube (102) during insertion of the elongated tube (102) into an externally accessible passageway of a patient.

9 Claims, 6 Drawing Sheets

NASAL

(56)                References Cited

U.S. PATENT DOCUMENTS

| | | | | |
|---|---|---|---|---|
| 5,058,577 | A * | 10/1991 | Six | A61M 1/84 |
| | | | | 128/207.14 |
| 5,235,970 | A * | 8/1993 | Augustine | A61M 16/04 |
| | | | | 128/207.14 |
| 5,919,183 | A * | 7/1999 | Field | A61M 16/0488 |
| | | | | 128/207.14 |
| 6,860,264 | B2 | 3/2005 | Christopher | |
| 7,243,653 | B2 * | 7/2007 | Nelson | A61M 16/04 |
| | | | | 128/207.14 |
| 7,650,886 | B1 * | 1/2010 | Keller | A61M 16/0493 |
| | | | | 128/207.14 |
| 8,505,531 | B2 | 8/2013 | Pecherer et al. | |
| 8,695,590 | B2 | 4/2014 | Parker | |
| 9,010,320 | B2 * | 4/2015 | Furman | A61M 16/0418 |
| | | | | 128/200.26 |
| 9,750,912 | B2 * | 9/2017 | McCormick | A61M 16/0488 |
| 10,080,854 | B1 * | 9/2018 | Pifer | A61M 16/0488 |
| 10,426,908 | B1 * | 10/2019 | Annis | A61M 16/0434 |
| 10,434,272 | B1 * | 10/2019 | Annis | A61B 1/267 |
| 10,569,039 | B2 | 2/2020 | Levitan | |
| 2004/0139972 | A1 * | 7/2004 | Wong | A61M 16/0418 |
| | | | | 128/207.14 |
| 2006/0207604 | A1 * | 9/2006 | Nelson | A61M 16/0443 |
| | | | | 128/207.14 |
| 2010/0307489 | A1 * | 12/2010 | Harms | A61M 16/0488 |
| | | | | 128/200.26 |
| 2010/0313894 | A1 | 12/2010 | Crumback et al. | |
| 2011/0023871 | A1 * | 2/2011 | Pacey | A61M 16/0486 |
| | | | | 128/200.26 |
| 2012/0055470 | A1 * | 3/2012 | Pecherer | A61B 1/267 |
| | | | | 128/200.26 |
| 2012/0078050 | A1 * | 3/2012 | Schwartz | A61B 1/267 |
| | | | | 128/200.26 |
| 2013/0211263 | A1 * | 8/2013 | Boedeker | A61M 16/0418 |
| | | | | 600/478 |
| 2014/0200405 | A1 * | 7/2014 | Atlas | A61M 16/0488 |
| | | | | 128/200.26 |
| 2015/0133741 | A1 * | 5/2015 | Gill | A61M 16/0463 |
| | | | | 128/200.26 |
| 2018/0110950 | A1 * | 4/2018 | Runnels | A61B 1/05 |
| 2019/0014980 | A1 | 1/2019 | Herskovic | |
| 2020/0368474 | A1 * | 11/2020 | Sun | A61M 16/0488 |
| 2021/0213224 | A1 * | 7/2021 | Venticinque | A61M 16/0418 |

FOREIGN PATENT DOCUMENTS

| | | | | | |
|---|---|---|---|---|---|
| JP | | 10033680 | A * | 2/1998 | A61M 16/0488 |
| WO | WO-2008138119 | A1 * | 11/2008 | | A61M 16/0488 |
| WO | | 2013188845 | | 12/2013 | |
| WO | WO-2017134284 | A1 * | 8/2017 | | A61M 16/04 |

* cited by examiner

NASAL

ORAL

AIRWAY MANAGEMENT DEVICE WITH CURVED STYLET

TECHNICAL FIELD

The present subject matter relates, in general, to the field of surgical instruments and methods, and more particularly to simple J-shaped stylet for airway management.

BACKGROUND

Airway management is one of the most important skills in the field of anesthesiology, and the inability to secure the airway may lead to catastrophic results. The airway of a human being includes the throat and windpipe and leads to the lungs. Control and management of a patient's airway are required under a variety of circumstances, for example, during the administration of general anesthesia. Control of a patient's airway is also necessary to permit mechanical ventilation of a patient with dysfunctional lungs and during resuscitation of a hemodynamically compromised and apneic or non-breathing patient. Mechanical ventilation of a patient involves forming a seal around some portion of the patient's breathing anatomy and introducing air that varies in pressure through the seal.

The air is provided through a tube from a ventilating machine. The seal confines the varying air pressure in the airway and lungs of the patient, imposing artificial respiration on the lungs. A breach in the seal undesirably lets the varying pressure escape to the ambient atmosphere, which inhibits airway management. Therefore, the quality and efficacy of an airway management device depend upon the seal that it forms where it interfaces with a patient's airway.

Nowadays varieties of airway devices are available for airway management. These devices are used from the oral/nasal route to accomplish the goal of securing the airway. In cases of a difficult airway, the preferred route for securing the airway is nasal, as it is a natural route of the respiratory process. In this regard, one of the enabling technologies to advance minimally invasive procedures are instruments and devices which are inserted through small openings and then expand elastically to a desired size and function. Today, there is no such device out of all commercially available airway devices, that can transform its shape and mold itself to pass through body orifices and thereafter "acutely recoil" its original shape completely, upon getting space within the body cavity to expand and perform the whole procedure in the reverse direction and get removed from the body.

Various prior art systems have been devised to overcome the aforementioned problem. In one prior art solution, disclosed is apparatuses useful in and methods for positioning of an endotracheal tube within an airway by allowing manual articulation of the endotracheal tube while a patient is being intubated. The apparatuses and methods are of particular use in intubating patients with unique anatomical conditions that make standard stylets inadequate for intubation. In one embodiment, an apparatus may comprise a stylet having a first end and a second end, with the second end of the stylet being insertable within a lumen of the endotracheal tube. First and second articulatable portions of the stylet may be independently articulated into respective primary and secondary arcuations to bend the endotracheal tube in conformance therewith as desired during the intubation procedure.

In another prior art solution, provided is an introducer for tracheal tube intubation has a proximal section connected to a distal section having an angled bougie tip. The introducer is configurable (i) for use as a bougie in which a tracheal tube is railroaded over the introducer's back end and into a trachea and (ii) for use as a stylet in which a tracheal tube is pre-loaded onto the introducer for insertion into a trachea. In certain embodiments, the introducer has one or more flexible or malleable sections that enable the introducer to bend into different configurations. The flexible/malleable sections have directional bending such that the sections bend in roughly the same plane as the angled bougie tip. This enables an operator always to know the orientation of the bougie tip even after it has been inserted into the trachea. The flexible/malleable sections enable the introducer to be configured with a handle or other type of grip.

In yet another prior art solution, provided is a stylet for providing access to an airway of a patient for insertion of an endotracheal tube for intubation is presented. The stylet is a hollow tube with a proximal and a distal end. The proximal end of the stylet has an actuator for, among other things, releasing the stylet when the ETT has been properly situated in the trachea of a patient. The stylet and bougie, if used, is removed prior to the balloon of the ETT being inflated to keep the ETT in the trachea. The stylet also is shaped prior to the insertion into the mouth and throat of the patient. The preformed shape of the stylet is consistent with the pathway to the trachea.

In another prior art solution, provided is a method and apparatus for endotracheal intubation with simultaneous oxygenation/ventilation employs a curved guide and a light wand to ensure proper placement of the endotracheal tube in the patient's airway. The light wand has an elongated flexible member with a light source at its distal tip. The wand is inserted through an endotracheal tube until the light is adjacent to the distal end of the endotracheal tube. A curved guide is inserted into the patient's mouth and upper airway so that its distal end is positioned above the larynx. The wand and endotracheal tube are then advanced along the guide until the distal end of the endotracheal tube passes through the larynx and the light source is externally observable at a predetermined location through the anterior tracheal wall.

Multitude of other literatures are also available on the management of difficult airway due to numerous pathologies and the different devices to be used in these cases, yet the brunt to secure the airway remains on the anesthetist in any given scenario. A simple and convenient device is necessary for intubation that can be handled by even a layman in emergencies.

Thus, there has always been a need for an airway device that is introduced through a nasal orifice and that is introduced into larynx without any/much manipulation, thereby controlling the airway in a fraction of time without the need for highly skilled experts for the procedure.

BRIEF DESCRIPTION OF DRAWINGS

The detailed description is described with reference to the accompanying figures. The accompanying drawing illustrates the embodiment of the invention and together with the following detailed description serves to explain the principles of the invention.

DETAILED DESCRIPTION

Figure 1:
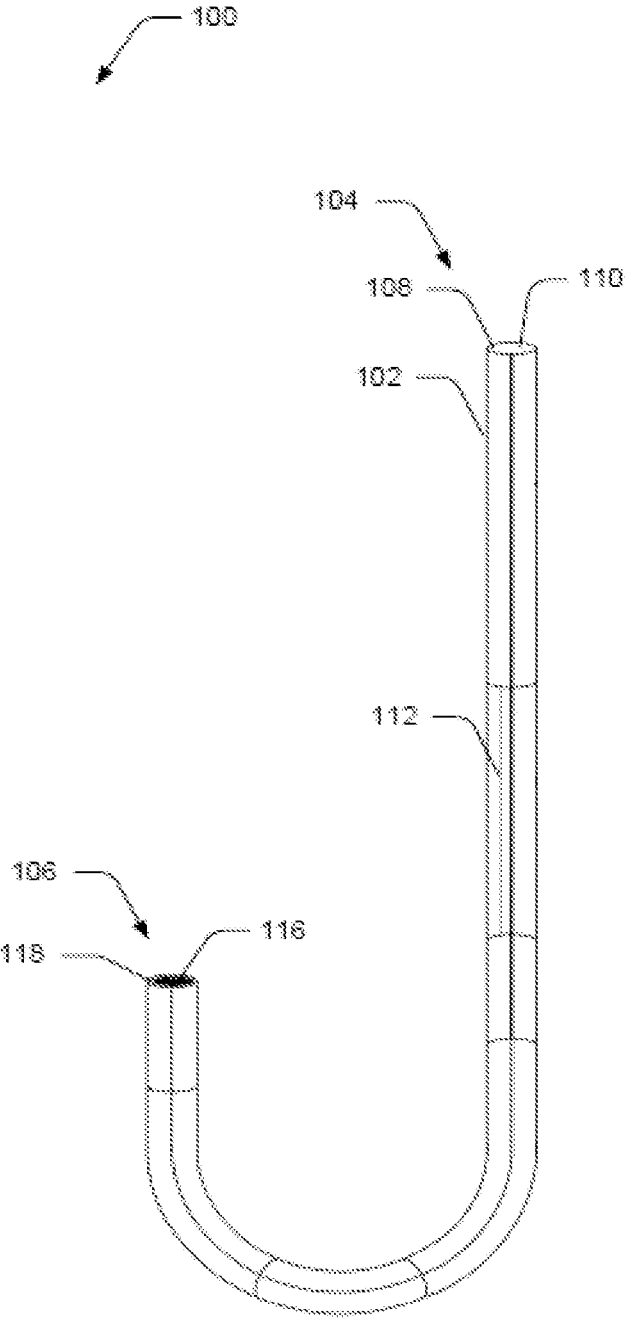
FIG. 1 illustrates an airway device having a stylet, according to an example embodiment of the present invention.

The present subject matter relates to aspects, relating to a J-shaped stylet that has a potential to change the standard method of intubation due to its flexibility, smaller diameter, less manipulation, and shorter intubation time, making the J-shaped stylet more acceptable for patient and medical personnel.

In an example embodiment, the present invention provides a simple J-shaped stylet which is pushed through the nose like a Nasogastric Tube (NGT) and will reach larynx as quickly as it is pushed, without further manipulations as compared to different available stylets or video stylets which require a lot of manipulation to mobilize their tips towards the larynx.

Nitinol is a well-known name in the field of medical engineering because Nitinol is being widely used in past three decades for a range of purposes, e.g., as orthodontic archwires, endoscopic instruments, orthopedics, radiology, guidewires and of course the most celebrated super-elastic medical device, a self-expanding metallic stent. But the use of Nitinol in anesthesiology has not been explored much except tracheal stents. The medical industry itself has been driven towards less and less invasive medical procedures, this in turn has created a demand for new medical devices that are not made with conventional materials.

The importance of Nitinol in the field of medicine has proven to be far greater than just as a simple "springy metal". Nitinol, conventionally, has been considered as a "material of choice" for applications requiring enormous flexibility and motion. The most leveraged advantage of Nitinol is super-elasticity, which is well known since the early 1970s. Super elastic Nitinol has become a material of strategic importance as it allows us to overcome a wide range of technical and design issues relating to the miniaturization of medical devices and therefore has widely been used in making medical devices that are used for less invasive and less traumatic procedures.

During medical procedures, the super-elasticity of the material helps a medical person to get the desired shape dynamically in time without extra manipulations. Nitinol is considered to have well documented super-elastic characteristics at room and around body temperature making it an ideal choice for a variety of medical device applications. Nitinol is used for its kink resistance and 'soft' end-user feel, therefore, allowing precise placement and delivery through very tortuous paths without losing a good torquability and pushability of the device.

Thus, it is understood that the airway device which is made from Nitinol is superplastic in the body yet martensitic when constrained and passed through nose/airway devices. There are various advantages relating to the super-elastic behavior, such as large recoverable deformation i.e. uniform plastic deformation; elastic and thermal deployment; low permanent set or residual deformation; high plateau stresses and ultimate tensile strength; body temperature within super elastic temperature range (i.e., 50.8 percent NiTi); high potential energy storage capability; hysteresis; corrosion resistance similar to stainless steel and titanium alloys; biocompatibility; kink or crush-resistance; flexibility; good fatigue life; generation of constant or low forces over a wide range of deformation; and MRI compatibility.

Moreover, Nitinol wires have been used in guidewires for their kink resistance, biased stiffness, and torquability since the early 1980s. The use of Nitinol has allowed for alleviating many intrinsic elastic limitations of stainless steel. Nitinol wire has an elasticity that is ten times more than that of stainless steel wire and because of this Nitinol can be bent several times more than stainless steel wire without permanent deformation. Just as the Nitinol is an exception in the field of metallurgy, stainless steel is less suitable for use in the field of biology. The extraordinary compliance of Nitinol makes it the metal most mechanically similar to biological materials.

Thus, there is a need for specific J shaped stylet wire prepared from a special biocompatible metal alloy Nitinol (NiTi).

In an example implementation of the present subject matter, the J-shaped stylet has been designed in a unique J shape that resembles a pathway of air from nose to larynx. This J-shaped stylet has been made from a specific super elastic alloy material Nitinol.

The above and other features, aspects, and advantages of the subject matter will be better explained with regard to the following description and accompanying figures. It should be noted that the description and figures merely illustrate the principles of the present subject matter along with examples described herein and, should not be construed as a limitation to the present subject matter. It is thus understood that various arrangements may be devised that, although not explicitly described or shown herein, embody the principles of the present disclosure. Moreover, all statements herein reciting principles, aspects, and examples thereof, are intended to encompass equivalents thereof. Further, for the sake of simplicity, and without limitation, the same numbers are used throughout the drawings to reference like features and components.

FIG. 1 illustrates a system 100 for managing an airway, in accordance with an implementation of the present subject matter. The system 100 comprises an elongated tube 102 having a proximal end 104, and a distal end 106, and defines a first lumen 108 that extends between the proximal end 104 and the distal end 106, wherein the first lumen 108 has a passageway. The elongated tube 102 further comprises a second lumen 110 that is positioned adjacent to the first lumen 108 and extends between the proximal end 104 and the distal end 106 and has passageway. The second lumen 110 also comprises a gas supply line that is adapted to supply the gas from a gas supply device to the passageway.

The system 100 for managing the airway further comprises a stylet 112 that is disposed partially into and removable from the first lumen 108, wherein the stylet 112 is used for steering and guiding the elongated tube 102 during the insertion of the elongated tube 102 into an externally accessible passageway of a patient.

In an example embodiment of the present subject matter, the stylet 112 may adjust the configuration of the elongated tube 102 during insertion into the passageway to conform to the configuration of the passageway and to enable the elongated tube 102 to slide easily into the passageway and allow the endotracheal tube to be railroaded over it and fit within the passageway of the patient after insertion and upon removal of the stylet 112 to leave the endotracheal tube in the passageway of the patient.

In another example embodiment of the present subject matter, the stylet 112 may have a distal tip 114 that remains curved and flexible in its neutral state. Further, the flexibility of the stylet 112 is variably stiffened and curved into a range of anatomic shapes that may be suitable to guide the elongated tube 102 from outside of the patient, through the externally accessible passageway, and is adjustable during use. Furthermore, the stylet 112 may move from a first position to a second position, within the first lumen 108, leaving the elongated tube 102 in a desired position.

Figure 2:
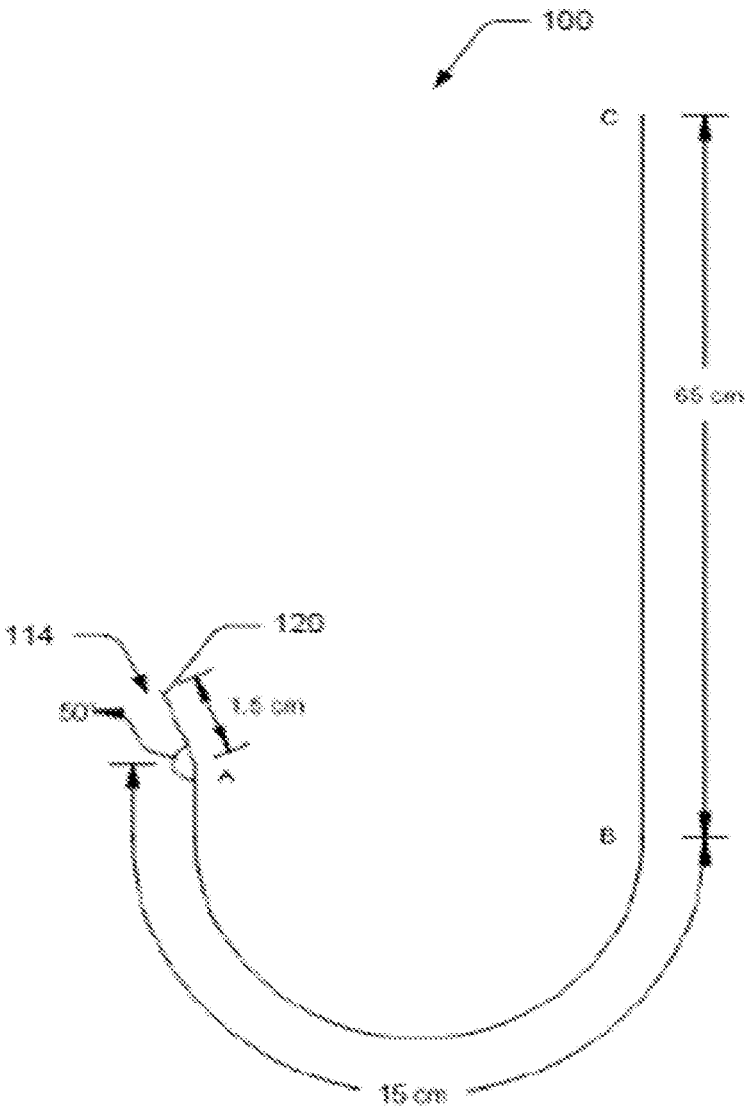
FIG. 2 illustrates another embodiment of an airway device having a stylet with a curved forward tip, according to an example embodiment of the present invention.

FIG. 2 illustrates another embodiment of a system 100 for managing an airway, in accordance with an implementation of the present subject matter. In an embodiment, straight length of the J-shaped stylet 112 may be 60-70 centimeters and curved forward length AB of the J-shaped stylet 112 may be in a range of 13-15 centimeters. As shown in FIG. 2, the curved forward length AB of the stylet 112 may be J-shaped, in accordance with an implementation of the present subject matter. Further, the J-shaped stylet 112 may be dispensed as disposable/reusable product which may have a thickness in a range of 0.5 to 0.7 millimeter for adults. For example, stylets that are made of thicker wires are less susceptible to buckling than fine wires, due to their lower slenderness ratio.

In an example embodiment, the J-shaped stylet 112 opening at the distal end looks like a pipe that has been cut off at an angle of roughly 50 degrees. Alternatively, this angle may be in a range of approximately 30 degrees to approximately 90 degrees. Further, it is to be noted that in FIG. 2, the tip has been cut at an angle of 50 degrees, wherein, the slashed portion may have a length in a range of 0.5-1.5 centimeters.

The J-shaped stylet 112 is made of a very small diameter wire and, therefore, is least likely to cause any trauma to tissue that may come in contact with the J-shaped stylet 112, unless an undue force is applied constantly to overcome spring-back action of the J-shaped stylet 112. During extubation removal of ETT over the J-shaped stylet 112 helps in maintaining stiff and less irritable conduit for anesthetists in anticipated reintubation e.g., difficult intubations, interdental wire fixation, tracheomalacia, etc. Even in ICU, it is a good practice to extubate over the J-shaped stylet 112.

The J-shaped stylet 112 is preferably, formed of a resilient and flexible material, i.e., medical-grade Nitinol which exploits the super-elastic property of Nitinol in its austenitic phase, to allow the large deformation compaction of a device into a small diameter NPA/SGAD/ETT for minimally invasive deployment in vivo. The J-shaped stylet 112 is unique in getting deformed to a maximum dimension during its passage through the nasal cavity and thereafter achieving a full return of shape when space is available and to reverse back in similar direction during withdrawal procedure without any extra efforts.

The J-shaped stylet 112 formed of Nitinol material may have additional advantages. In an example embodiment, "no learning curve" is required for using the J-shaped stylet 112, and some patients can be intubated without direct laryngoscopy. In another example embodiment of the present invention, few cases of awake intubation by the J-shaped stylet 112 may not require any oral instrumentation and thereby prevent all associated complications of laryngoscopy including "pressor response". Even those persons who are not accustomed to operating an airway device can easily use the J-shaped stylet 112. Operating the J-shaped stylet 112 is so quick and simple that it takes less than a minute to control a patient's airway.

As shown in FIG. 2, the J-shaped stylet 112 may have a raised segment 120, at the distal end 106, wherein the raised segment 120 forms a predetermined angle with the distal end 106 of the J-shaped stylet 112. The predetermined angle value may be in range of about 30-90 degrees. Further, the raised segment 120 may have a length in a range of 0.5-1.5 centimetres.

Though the airway device in an example embodiment of the present invention is made from a specific super-elastic alloy material Nitinol, those skilled in the art will understand that the airway device can also be made from any other super-elastic alloys such as Copper-Zinc-Aluminium (CuZnAl), Copper-Aluminium-Nickel (CuAlNi), Copper-Aluminium-Beryllium (CuAlBe), Ferrous-Manganese-Silica (FeMnSi), Ferrous-Nickel-Cobalt-Titanium (FeNiCoTi), Ferrous-Nickel-Cobalt-Aluminium (FeNiCoAl), Ferrous-Nickel-Cobalt-Aluminum-Tantalum (FeNiCoAlTa), Titanium-Niobium-Tantalum (TNT-Ti-17Nb-6Ta), and Nickel-Titanium (NiTi).

Figure 3:
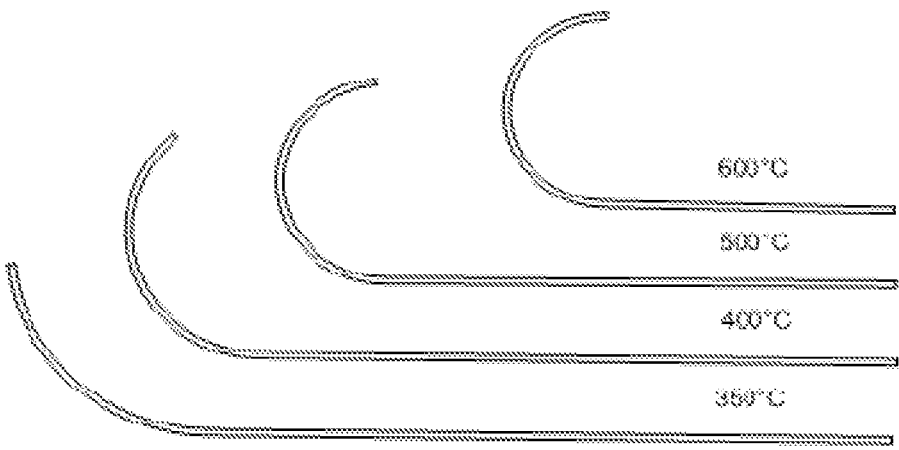
FIG. 3 illustrates the shape variation of Nitinol wire at different temperature ranges according to an example embodiment of the present invention.

FIG. 3 illustrates a Nitinol wire that is shaped into hooks and heat-treated at 350° C., 400° C., 500° C., and 600° C. for 5 minutes. In another example, the heat-treating time may be in in a range of 1 to 600 seconds. It is noted that the hook shape is optimized at the higher temperatures.

As discussed earlier, the J-shaped stylet 112 is made from medical grade Nitinol, which comprises near equal atomic weight percentage of Nickel (Ni) and Titanium (Ti), a chemistry requirement set forth by ASTM F2063 (Standard Specification for Wrought Nickel-Titanium Shape Memory Alloys for Medical Devices and Surgical Implants). To fix the original "parent shape", the alloy must be held in a position and heated to about 500° C. (932° F.). This process is usually called a shape setting. J-shaped arch of Nitinol wire is a specific design, which is achieved from straight superelastic Nitinol wire that undergoes a specific shape setting with repeated heat (in a range 500° C.-600° C.) and cold works to finally achieve its assigned shape.

In an example implementation of the present subject matter, in order to improve lubricity, the J-shaped stylet 112 may be coated with Teflon or a hydrophilic coating and employ a helical wrap to improve radio-opacity at the distal tip of the J-shaped stylet 112. Also, the J-shaped stylet 112 is marketed as a disposable item or reusable item where the J-shaped stylet 112 may be sterilized by dipping in CIDEX/Sodium hypochlorite solution. Alternatively, Poly-vinyl Chloride (PVC) tubing also be employed or worn over the wire every time and reuse the wire as it is not exposed to body secretions. In accordance with an embodiment of the invention, the J-shaped stylet 112 may be sterilized by Ethylene oxide sterilization (ETO).

Figure 4:
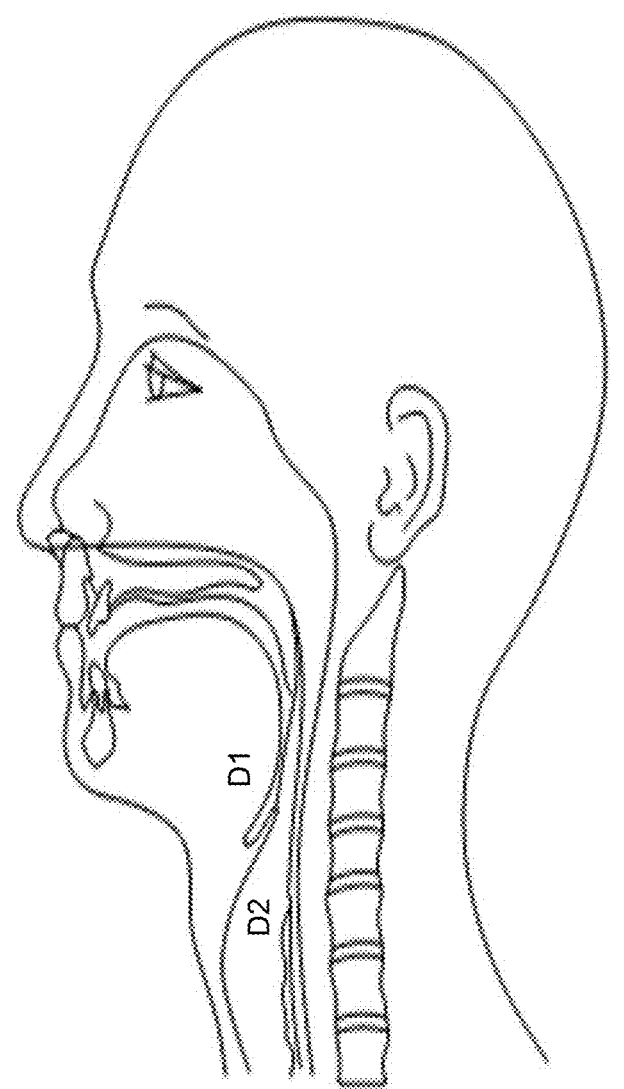
FIG. 4 illustrates side cross-sectional representations of the anatomy of the nose showing the introduction and positioning of the airway device of FIG. 1 according to an example embodiment of the present invention.

FIG. 4 is a schematic diagram for measurement of the nares-to-epiglottis distance D1 and the nares-to-vocal cords distance D2. FIG. 4 also shows a schematic side cross-sectional representation of the anatomy of the nose showing the introduction and positioning of the J-shaped stylet 112 which usually lies in portion between points A and B of FIG. 2.

The specific J-shaped arch of the Nitinol superelastic wire has an anatomical advantage, such that when introduced through nose, the J-shaped stylet 112 comes out of the nasopharynx into the posterior part of the oropharynx and move towards the hypopharynx into laryngopharynx. As shown in FIG. 4, the J-shaped stylet 112 anatomically aligns to the base of tongue and epiglottis and the tip of the J-shaped stylet 112 comes to rest very near to the vocal cords and below the epiglottis without any big manipulations.

The 30-degree anterior curve may help in lifting the epiglottis gently by applying pressure and the tip enters smoothly into the trachea between vocal cords. Further manipulation of the J-shaped stylet 112 may cause the arch-wire to gently straighten up inside the trachea. The opposite curve of the tip and the J arch maintain pressure in opposite directions and thereby nullify the individual pressure effect and thus avoid any pressure damage to the tracheal wall mucosa during the railroading of ETT over the J-shaped stylet 112. The smaller diameter (0.5/0.7 millimetres) of the stylet wire may allow the J-shaped stylet 112 to pass through small orifices and ETT of different sizes during or in between the procedure of endotracheal intubation, and that is why it works as an ideal airway exchange stylet.

Further, the superelastic nature of the J-shaped stylet 112 may allow the J-shaped stylet 112 to rebound to its original shape without requiring any manipulations, even if any obstacle (obstruction) comes in the path of the J-shaped stylet 112 and tries to distort the shape of the J-shaped stylet 112.

The anterior curvature, in a range of 0.5-1.5 centimeter on the tip of the J-shaped stylet may help the J-shaped stylet 112 to properly point itself towards the laryngeal inlet and also assist in lifting the epiglottis (as if opening a shutter to expose vocal cords) to get a better view of the larynx. The J-shaped stylet 112 has been designed in such a way that it makes it possible to use the J-shaped stylet 112 as airway intubator.

The modulus of elasticity is biased, substantially more in the loading direction than in the unloading direction. The result is that superelastic devices resist deformation with much greater force than the force they apply passively to surrounding tissue, this property is beneficial in the J-shaped stylet by helping lift the epiglottis without much pressure on the J-shaped stylet and the surrounding hypopharynx. In commercially available malleable stylets, one has to alter the shape of the stylet and then introduce the stylet in body, wherein the shape of the stylet gets deformed while passing through torturous body pathways.

Advantageously, the unique "J" curve design and strong, flexible wire has an added advantage that the J-shaped stylet 112 may be repositioned quickly and, as often as necessary, may achieve accurate placement without permanently distorting the J-shaped stylet 112 or requiring the J-shaped stylet 112 to be removed in between the procedure for reshaping. Due to super-elastic material the J-shaped stylet 112 may be curled up in a laryngoscope bag and easily unwinded when needed without deforming/destroying the specific J-shaped curve of the J-shaped stylet 112, thereby, making the J-shaped stylet most handy instrument for use by all airway managing physicians.

In an example, the J-shaped stylet 112 may be considered as a relatively noninvasive airway tool that causes minimal risk of tissue compression and thereby, minimal disturbance of the cardiovascular and respiratory system. The J-shaped stylet 112 has the easiest insertion in various types of manikins. Advantageously, easy insertion technique, no manipulation during the procedure for changing its dynamic shape and friendly neighborhood to airway anatomy makes use of the J-shaped stylet 112 by novice, equally successful without a learning curve.

In an example embodiment, the J-shaped stylet 112 may be used as a rescue airway device in an emergency as well as an elective setting. The J-shaped stylet 112 may also be an established part of routine airway management and may be extremely useful in managing the difficult airway. The J-shaped stylet 112 may also be used as a new armamentarium in difficult airway cart and may work both as a ventilatory device (as airway-when provided with dual lumen tube set) and a conduit for endotracheal intubation.

In another example embodiment, the J-shaped stylet 112 may be used with any kind of direct or video laryngoscope (channeled/un-channeled) or with video stylets for an easy, smooth, and confirmed intubation with proficiency and without any hassle. In patients on TIVA (Total IV Anesthesia) or MAC (Monitored Anesthesia Care) sedation with nasal airway in situ, the introduction of the J-shaped stylet assembly may help in curving the airway more towards the laryngeal inlet and thereby maintaining better oxygenation. Even a reinforced endotracheal tube (ETT) may be easily negotiated through the nose via J-shaped stylet 112 because of the flexibility of the J-shaped stylet 112. The anatomical pathway of breathed air may be a shape acquired by the J-shaped stylet 112 while passing from the nose towards larynx and due to this natural course, the J-shaped stylet 112 may have a more chance of reaching larynx than all other modalities for blind nasal intubation techniques.

In an exemplary embodiment of the present invention, clinical experience has shown that direct blind intubation has approximately 55 percent success rate with Laryngeal mask airway (LMA), however, this may be further improved with J-shaped wire technique over LMA. Because of the super-elastic nature of the J-shaped stylet 112, it is least possible to create trauma/false passage while introducing blindly, and J-shaped stylet 112 may bounce back if any obstacle comes in the path of the J-shaped stylet 112. The J-shaped stylet 112 only proceeds forward if there is a space available for the tip of the J-shaped stylet 112 to pass along forwardly.

Due to all unique material properties and specifically assigned J shape, with the ease of use by any novice, the J-shaped stylet 112 may be employed advantageously in difficult airway cart and difficult airway algorithm. Theoretically, in difficult airway algorithms worldwide, the J-shaped stylet 112 may become steadfast in all steps of securing the airway including surgical access (FONA—Front-of-neck access) wherein, the J-shaped stylet 112 is threaded through a cricothyroid needle into the trachea and thereafter railroad an ETT over the J-shaped stylet 112.

Similarly, the J-shaped stylet 112 may be useful in retrograde intubation as a more invasive airway securing technique. Digital intubation is also consummated by the J-shaped stylet 112. The J-shaped stylet 112 may also act as a secure airway conduit in cases of apnoeic oxygenation.

In an example embodiment, a laryngotracheal mucosal atomization device is also made from this J-shaped arch-wire, so that the purpose of spraying the local anesthetic drug over the larynx is more aptly achieved before performing awake bronchoscopy. The J-shaped stylet 112 may be used during Cardio-Pulmonary Resuscitation (CPR) due to the high success rate of intubation in the first attempt along with quick insertion time. Also, easy intubation during chest compression has an additional advantage for all Emergency Medical Service (EMS) providers. Problems during intubation like arterial desaturation and hemodynamic changes are not likely, due to shorter time for successful intubation aided by J-shaped stylet 112.

In an example embodiment of the present subject matter, the system 100 may be provided with an imaging device 116 that may be coupled to the distal end 106 of the J-shaped stylet 112. The system may further comprise an illumination device 118 that may be disposed at distal end of the imaging device 116. The system 100 may also comprise an image processor (not illustrated) that may be coupled to the proximal end 104 of the stylet 112, wherein the imaging processor is electrically connected with the imaging device 116. The system may additionally be provided with a display (not illustrated) that may be configured to present a real time video image of the view in front of the distal tip 114 of the J-shaped stylet 112 as the J-shaped stylet 112 is introduced into the elongated tube 102 and inserted into the airway of the patient. Further, the illumination device 118 may include one or more LEDs. Further, a defogging solution may be wiped on the imaging device 116 to maintain clear viewing.

In alternative embodiments, the imaging device 116 and the illumination device 118 may be are powered from a peripheral source or are powered by means of a self-contained power source pack. It is the purpose of the invention herein to provide a means of intubation, facilitated by an optical system, in those types of patients whose pharynx, larynx and trachea are not easily visualized.

An additional unique attribute of J-shaped arched Nitinol wire is that they have shape memory effect too. The J-shaped stylet 112 may be used in following other anesthetic products; Nasal endotracheal tubes may be reinforced with the J-shaped stylet 112 to achieve easy and fast intubation without the aid of a Magill forceps; Nasal airways may be reinforced with the J-shaped stylet 112 for better anatomical curve and better oxygenation of patient, even when their size is incongruent to the patient; the laryngotracheal atomization device may be incorporated with the J-shaped stylet 112, so that the laryngotracheal atomization device is more aligned to spray the drug over the laryngeal inlet; an endoscope camera with light at tip of the wire may make the J-shaped stylet 112 smart, slimmest and most flexible video stylet; the J-shaped stylet 112 may also be dispensed with a dual lumen tube, where the J-shaped stylet 112 is introduced through one tube and the other tube works as an oxygen supplying cannula, thereby maintaining oxygenation of the patient till the airway is secured; a LED light at the tip of the J-shaped stylet 112 may make the J-shaped stylet 112 a smart light wand and aid in fast blind nasal intubation.

In an example embodiment, the J-shaped stylet 112 may have a different pediatric version of the stylet with a design quite similar to the adult version, but with smaller dimensions. For the pediatric version, the J-shaped stylet 112 may be dispensed as a disposable/reusable product that has a thickness that is less than 0.7 millimeters. This is because 0.7 millimeters stylet is for use with obese and large-sized patients. It has a slightly different distal part for orally used J Stylet wire.

The J-shaped stylet 112 is "one in all" guidewire, useful for intubation among all available anesthesia instruments to date. It is used by conventional anatomical routes (oral/nasal) for securing the airway and also equally effective in unconventional (FONA/retrograde intubation) methods of securing the airway. The J-shaped stylet 112 may be considered as a simple, smart, and easy to use airway device. It is easy to insert without the need for any manipulations with the maintenance of the airway in a short time. It is a single stop solution for intubation with any type of laryngoscopes, Supraglottic Airway Device (SGAD), airways, digital intubation, and even blind intubation techniques. The J-shaped stylet 112 may be very effective and useful for adult patients especially in awake blind nasal intubation. The J-shaped stylet 112 may be used advantageously because the J-shaped stylet 112 has qualities of speedy yet successful insertion, ventilation, and intubation. The J-shaped stylet 112 may be useful in all the steps of any difficult airway algorithm and in extubation algorithms where the J-shaped stylet 112 may act as a conduit and Airway Exchange Catheter (AEC).

Another additional advantage is that the camera version of the J-shaped stylet 112 may be used to intubate the patient without the use of any other instrument at hand and in that scenario the J-shaped stylet is equivalently useful as an Automated External Defibrillator (AED) machine. A novice not only can do a cardiac resuscitation but also real-time intubations even for the first time without extra knowledge of airway/devices.

Indications

All indications of nasal intubation, including awake and blind nasal technique. The primary design goal of the J-shaped stylet 112 is to aid (blind) tracheal intubation.

The J-shaped stylet 112 may produce an intubating system that eliminates the need for anatomical distortion and does not require manipulation of the head and neck, and thus increases the utility of the J-shaped stylet 112 in patients with cervical spine pathology with/without the cervical collar in situ.

The J-shaped stylet 112 of the present invention may be very useful in the management of the difficult airway. The J-shaped stylet 112 works as a rescue airway when used with nasal airway in "cannot intubate, can ventilate" and "cannot intubate, cannot ventilate" scenario.

The J-shaped stylet 112 may act as a perfect Airway Exchange Catheter.

The J-shaped stylet 112 may also be used as a difficult airway extubation conduit device over which an ETT is removed, yet keeping the airway secured by the J-shaped stylet 112 and also providing oxygenation simultaneously, especially in difficult intubation cases. Also, the J-shaped stylet 112 may be very useful device in cases of severe laryngeal edema or tracheal stenosis for maintaining oxygenation till an ideal airway is secured.

Insertion Technique

Figure 5:
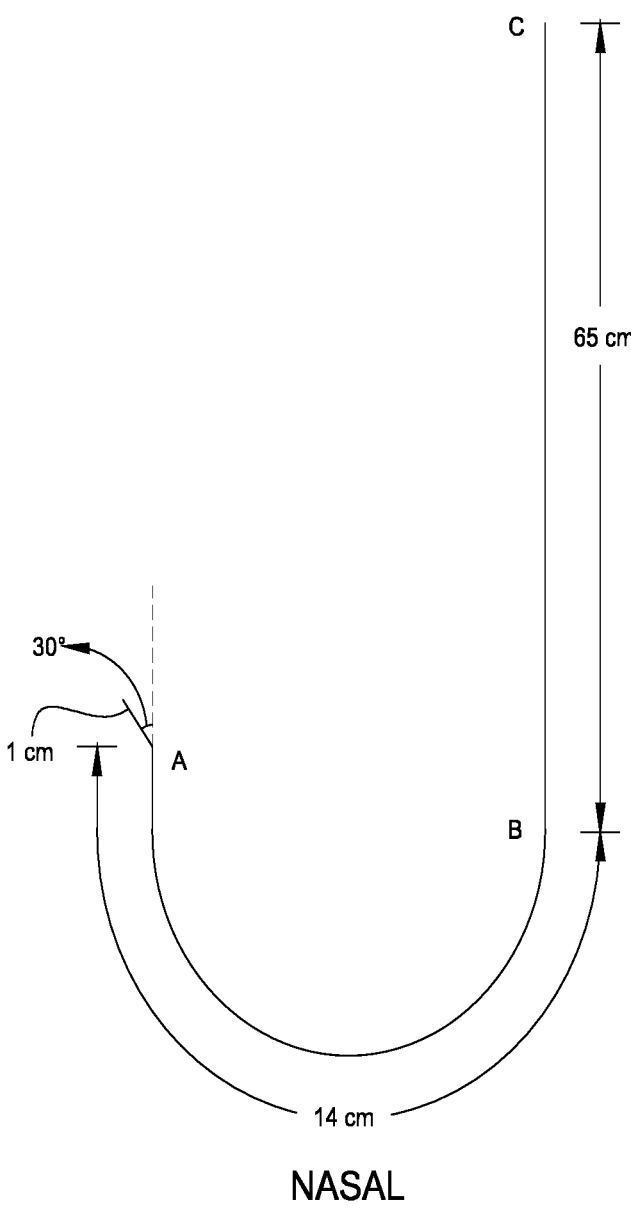
FIG. 5 illustrates a nasal J-shaped stylet according to an example embodiment of the present invention.
Figure 6:
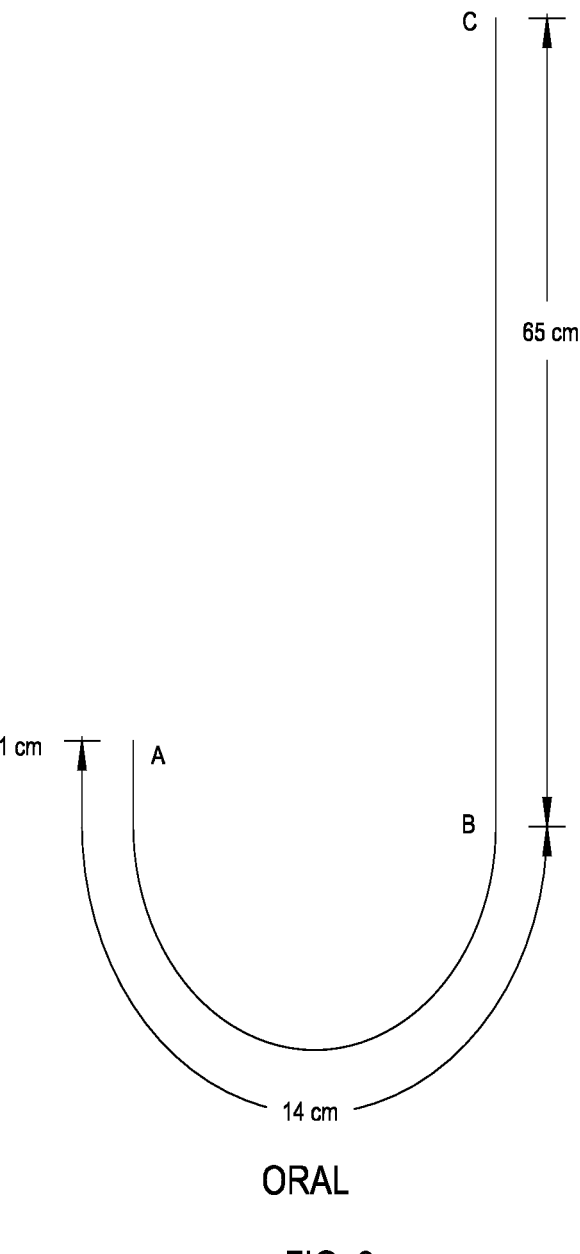
FIG. 6 illustrates an oral J-shaped stylet according to an example embodiment of the present invention.

The J-shaped stylet 112 may be considered as a relatively non-invasive device for airway intubation and occasional maintenance. In emergencies the J-shaped stylet 112 may be introduced without the use of a laryngoscope or muscle relaxants. In an embodiment, as shown in FIG. 5, the J-shaped stylet 112 may be introduced by nasal (preferred) or, as shown in FIG. 6, the J-shaped stylet 112 may be introduced through oral route and the outer diameter of the J-shaped stylet 112 permits the use of the J-shaped stylet 112 with any available laryngoscope, airways as well as SGAD. The J-shaped stylet 112 may be used in a supine position with head straight/turned on one side, sitting and semi-sitting positions. The use of a J-shaped stylet 112 may be equally effective in a prone position.

Nasal

With the patient lying supine, the J-shaped stylet 112 may be introduced with an arch of the J-shaped stylet 112 facing through the external nares, as illustrated in FIG. 5. The J-shaped stylet 112 may align to the airway anatomy and abuts to hard palate followed by the soft palate and thereafter curve down behind the soft palate to come out through the nasopharynx into the posterior part of the oropharynx and then due to superelasticity of the J-shaped stylet, the J-shaped curve tries to revert to its original shape due to the available space within the oropharynx.

This acute recoil of the J-shaped stylet 112 may lift the tip of the J-shaped stylet 112 and in the hypopharyngeal area it may reach towards epiglottis and laryngeal inlet. In anesthetized patient, the tongue falls back and presses upon the wire to straighten it up, but the superelastic nature of the J-shaped stylet wire overcomes that strain and maintain the original shape of the J-shaped stylet 112 as much as it can to keep the tip upwards towards epiglottis. In these circumstances one needs to give a jaw thrust to move the tongue up and open the space in pharynx and hypopharynx.

In an embodiment, as shown in FIG. 4, the nares-to-epiglottis distance A may be in a range of approximately 11-15 centimetres and nares-to-vocal cords distance B may be in a range of approximately 15-20 centimetres.

In another embodiment, the J-shaped stylet 112 may be passed through a nasopharyngeal airway, which results in an atraumatic bloodless view in the oropharynx and laryngopharyngeal area. The philtrum-to-ear tragus distance (PTD) is the best measurement to predict the optimal insertion depth of a nasopharyngeal airway and its appropriate size to be selected accordingly. It is known to the person skilled in that art that the distance from the nares to epiglottis (NED) is useful for blind nasotracheal intubation. The measurements of PTD differ from optimal insertion length (NED-1) by less than 1 centimeter for most patients.

Estimation of the nares-to-epiglottis and nares-to-vocal cords distances may facilitate the selection of properly sized nasopharyngeal airways and appropriate positioning of the J-shaped stylet 112.

In a planned awake blind nasal intubation, the airway of about PTD size or 1 size lesser is introduced and the J-shaped stylet is passed through the airway, which achieves a perfect direction for stylet tip to enter the larynx. In blind nasal intubation, the J-shaped stylet 112 may be placed into a small gauge lumen of a double-lumen tube and attach an EtCO$_2$ gas analyzer tube at the proximal end of another lumen of the same tube and thereby diagnose the correct placement of this assembly.

Oral

The J-shaped stylet 112 has efficiently been used via an oral route through oropharyngeal airway or other devices. Also, the blind intubation via oral route using the J-shaped stylet 112 may alone produce equally effective results.

Blind oral intubation through an SGAD is best achieved by the J-shaped stylet 112 due to extreme flexibility of wire that allows the J-shaped stylet 112 to mold its shape through tortures passage and reach into the trachea and thereafter the SGAD is removed over the J-shaped stylet 112 and an ETT is railroaded over the J-shaped stylet 112.

In oral intubation, the J-shaped stylet 112 may be passed through the oral airway to align to the natural anatomical shape and utilize the superelastic property of the J-shaped stylet 112 to recoil once the J-shaped stylet 112 comes out from the distal end of the airway, this helps the J-shaped stylet to enter the larynx uneventfully.

With direct or video laryngoscope, we can directly visualize the placement of the J-shaped stylet 112 in the trachea and thereafter railroad an appropriate size ETT over it into the trachea and confirm with standard methods of diagnosing tracheal tube placement. In an exemplary embodiment of the present invention, the oral J-shaped stylet 112 may only have the anterior big curve, however, the small anterior curve of the nasal J-shaped stylet 112 may be absent in the oral J-shaped stylet 112. Therefore, the oral J-stylet 112 may be 0.5-1 centimetres smaller than the nasal J-shaped stylet 112.

Further, by adequate measurement of the average arch size of the upper or lower jaw in any species, a specific stylet for said species can similarly be prepared which is beneficial to veterinary doctors who need to intubate their patients.

Also provided is a method for managing an airway, in accordance with an embodiment of the present disclosure. The method comprises the step of inserting an elongated tube 102 into an externally accessible passageway of a patient, wherein the elongated tube 102 includes a proximal end 104, and a distal end 106. The elongated tube 102 defines a first lumen 108, extending between the proximal end 104 and the distal end 106 and having a passageway. The elongated tube 102 further comprises a second lumen 110 that is positioned adjacent to the first lumen 108, extending between the proximal end 104 and the distal end 106, having a passageway. The second lumen 110 is having a gas supply line, wherein the gas supply line is adapted to supply gas from a gas supply device to the passageway.

Further, the J-shaped stylet 112 is disposed at least partially into and removable from the first lumen 108 and wherein the stylet 112 is used for steering and guiding the elongated tube 102 during insertion of the elongated tube 102 into the externally accessible passageway of the patient.

Although the subject matter has been described in considerable detail with reference to certain examples and implementations thereof, other implementations are also possible. As such, the present disclosure should not be limited to the description of the preferred examples and implementations contained therein.

I claim:

1. A system (100) for managing an airway, comprising:
an elongated tube (102) having a proximal end (104) and a distal end (106), the elongated tube (102) comprising:
a first lumen (108) extending between the proximal end (104) and the distal end (106), the first lumen (108) has a first passageway; and
a second lumen (110) positioned adjacent to the first lumen (108) extending between the proximal end (104) and the distal end (106), the second lumen (100) having a second passageway, wherein the second lumen (110) has a gas supply line, and wherein the gas supply line is adapted to supply gas from a gas supply device to the second passageway; and
a wire stylet (112) made of a shape memory alloy material and disposed at least partially into and removable from the first lumen (108), wherein the stylet (112) has a diameter in the range of 0.5 to 0.7 millimeters, wherein the stylet (112) is configured to steer and guide the elongated tube (102) during insertion of the elongated tube (102) into a nasal cavity through a nasal orifice of a patient, wherein the stylet (112) consists of:
a curved segment having a curved length (AB) extending from a distal first end (A) to a proximal second end (B);
a straight segment having a straight length (BC) extending from the second end (B) to a third end (C), wherein the curved segment and the straight segment of the stylet (112) are configured to form a J-shape in a neutral state of the stylet (112), configured to deform while passing through the nasal cavity, and configured to return to the J-shape when space is available inside a hypopharyngeal area; and
a bent segment (120) of a predetermined length formed at the first end (A) of the curved segment, wherein the bent segment (120) in the neutral state is oriented at a predetermined angle and extends away from the straight segment of the stylet (112), to allow the stylet (112) to point itself towards a laryngeal inlet of the patient and to assist in lifting an epiglottis in the hypopharyngeal area during recoil of the stylet (112), and to cause the stylet (112) to move smoothly into a trachea between vocal cords and to get a better view of a larynx when inserted into the nasal cavity;

wherein, in the neutral state of the stylet (112), the curved segment is curved 180° such that a distal portion of the curved segment extends substantially parallel to the straight segment.

2. The system (100) of claim 1, wherein the stylet (112) is configured to shape configuration of the elongated tube (102) during the insertion to conform to the nasal cavity to slide the elongated tube (102) into the nasal cavity and fit within the nasal cavity of the patient after insertion, wherein the stylet (112) is configured to railroad the elongated tube (102) over the stylet (112) and, upon removal, the stylet (112) is configured to leave the elongated tube (102) in the nasal cavity of the patient.

3. The system (100) of claim 1, wherein the stylet (112) is configured to be displaced from a first position to a second position within the first lumen (108), the first position being a location near the proximal end (104) of the first lumen (108) where the stylet (112) is initially placed for the insertion of the elongated tube (102) into the nasal cavity of the patient, and the second position being a location towards the distal end (106) of the first lumen (108) where the stylet (112) is displaced within the first lumen (108) to conform the elongated tube (102) to the shape of the nasal cavity of the patient.

4. The system (100) of claim 1, wherein the curved length (AB) of the stylet (112) is in a range of 13-15 centimetres, the straight length (BC) of the stylet (112) is in a range of 60-70 centimetres.

5. The system (100) of claim 1, wherein the stylet (112) is at least one of a disposable and reusable product.

6. The system (100) of claim 1, wherein the predetermined angle is in a range of 30 degrees to 90 degrees, and wherein the predetermined length of the bent segment (120) is in a range of 0.5-1.5 centimetres.

7. A wire stylet (112) for insertion of an endotracheal tube for intubation of a patient, wherein the stylet (112) is made of a shape memory alloy material, wherein the stylet (112) has a diameter in the range of 0.5 to 0.7 millimeters, wherein the stylet (112) is configured to be inserted into a nasal cavity of a patient through a nasal orifice of the patient, and the stylet (112) consists of:

a curved segment having a curved length (AB) extending from a distal first end (A) to a proximal second end (B), wherein the stylet (112) is configured to be inserted into a nasal cavity of a patient through a nasal orifice of the patient;

a straight segment having a straight length (BC) extending from the second end (B) to a third end (C), wherein the curved segment and the straight segment of the stylet (112) are configured to form a J-shape in a neutral state of the stylet (112), configured to deform while passing through the nasal cavity, and configured to return to the J-shape when space is available inside a hypopharyngeal area; and a bent segment (120) having a predetermined length smaller than the curved length (AB) and extending from the first end (A) of the curved segment, wherein the bent segment (120) in the neutral state of the stylet (112) is oriented at a predetermined angle and extends away from the straight segment of the stylet (112), to allow the stylet (112) to point itself towards a laryngeal inlet of the patient and to lift an epiglottis in the hypopharyngeal area during recoil of the stylet (112) thereby providing a better view of a larynx, and to cause the stylet (112) to move smoothly into a trachea between vocal cords;

wherein, in the neutral state of the stylet (112), the curved segment is curved 180° such that a distal portion of the curved segment extends substantially parallel to the straight segment.

8. The stylet (112) of claim 7, wherein the curved length (AB) of the stylet (112) is in a range of 13-15 centimetres, the straight length (BC) of the stylet (112) is in a range of 60-70 centimetres.

9. The stylet (112) of claim 7, wherein the predetermined angle is in a range of 30 degrees to 90 degrees, and wherein the predetermined length of the bent segment (120) is in a range of 0.5-1.5 centimetres.

* * * * *